United States Patent [19]

Wehner et al.

[11] 4,285,856
[45] Aug. 25, 1981

[54] ORGANO-TIN COMPOUNDS, PROCESS FOR THEIR PREPARATION AND THEIR USE

[75] Inventors: Wolfgang Wehner, Zwingenberg; Gerd Abeler, Darmstadt, both of Fed. Rep. of Germany

[73] Assignee: Ciba-Geigy Corporation, Ardsley, N.Y.

[21] Appl. No.: 118,898

[22] Filed: Feb. 6, 1980

[30] Foreign Application Priority Data

Feb. 14, 1979 [CH] Switzerland ............... 1467/79

[51] Int. Cl.$^3$ ..................... C07F 7/22; C08K 00/00
[52] U.S. Cl. ..................... 260/45.75 S; 260/429.7
[58] Field of Search ............... 260/429.7, 45.75 S

[56] References Cited

U.S. PATENT DOCUMENTS

| | | | |
|---|---|---|---|
| 4,080,363 | 3/1978 | Hutton et al. | 260/429.7 X |
| 4,202,830 | 5/1980 | Korbanka et al. | 260/429.7 |
| 4,210,595 | 7/1980 | Wirth et al. | 260/429.7 |

*Primary Examiner*—Helen M. S. Sneed
*Attorney, Agent, or Firm*—Luther A. R. Hall

[57] ABSTRACT

Compounds of the formula (I)

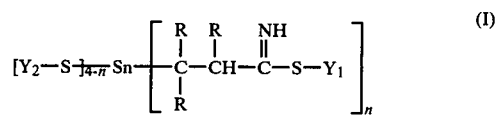

(I)

in which the radicals R independently of one another are hydrogen or $C_1$–$C_4$ alkyl and $Y_1$ and $Y_2$ are both identical and are $C_1$–$C_{20}$ alkyl, $C_2$–$C_{20}$ alkenyl, $C_5$–$C_8$ cycloalkyl, $C_6$–$C_{10}$ cycloalkylalkyl, $C_6$–$C_{14}$ aryl, which is unsubstituted or substituted by $C_1$–$C_8$ alkyl, or $C_7$–$C_{20}$ aralkyl or —$(CH_2)_m$—COO ($C_{1-4}$alkyl), or if $Y_1$ is —$(CH_2)_m$—COO—($C_{1-4}$alkyl), $Y_2$ can also be the group —$(CH_2)_m$—COO($C_{5-20}$alkyl), and in which m is a number from 1 to 6 and n is 1 or 2.

The compounds are heat stabilizers for halogen-containing thermoplastics.

9 Claims, No Drawings

ORGANO-TIN COMPOUNDS, PROCESS FOR THEIR PREPARATION AND THEIR USE

The present invention relates to carbofunctional mono- and di-organo-tin compounds, a process for their preparation and their use.

Organo-tin compounds enjoy considerable economic interest as stabilisers for halogen-containing thermoplastics. However, the characteristics still leave something to be desired in respect of stabilisation to heat.

Accordingly, a novel category of organo-tin compounds has been found which contain iminothioethers as the functional group and which no longer have the disadvantages of the comparable compounds known from the prior art. The novel compounds are obtainable in a simple manner, economically in high yields and under very mild reaction conditions. Easily accessible and inexpensive raw materials can be used as the starting materials.

The present invention thus relates to compounds of the formula (I)

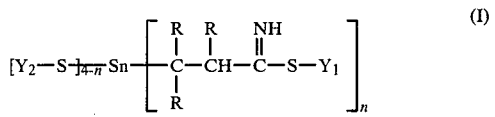

in which the radicals R independently of one another are hydrogen or $C_1$–$C_4$ alkyl and $Y_1$ and $Y_2$ are both identical and are $C_1$–$C_{20}$ alkyl, $C_2$–$C_{20}$ alkenyl, $C_5$–$C_8$ cycloalkyl, $C_6$–$C_{10}$ cycloalkylalkyl, $C_6$–$C_{14}$ aryl, which is unsubstituted or substituted by $C_1$–$C_8$ alkyl, or $C_4$–$C_{20}$ aralkyl or —$(CH_2)_m$—COO ($C_{1-4}$ alkyl), or if $Y_1$ is —$(CH_2)_m$—COO—($C_{1-4}$ alkyl), $Y_2$ can also be the group —$(CH_2)_m$—COO($C_{5-20}$ alkyl), and in which m is a number from 1 to 6 and n is 1 or 2.

R is hydrogen or $C_1$–$C_4$ alkyl, such as methyl, ethyl, iso-propyl or n-butyl, preferably hydrogen or methyl and in particular hydrogen.

$Y_1$ and $Y_2$ can be $C_1$–$C_{20}$ alkyl and the alkyl can be linear or branched, for example methyl, ethyl, i-propyl, n-butyl, 2-ethylhexyl, n-dodecyl, n-tetradecyl or octadecyl. Alkyl having 8–20 C atoms is preferred, such as 2-ethylhexyl, n-dodecyl or n-tetradecyl, in particular n-tetradecyl.

$Y_1$ and $Y_2$ can be $C_2$–$C_{20}$ alkenyl, for example vinyl, allyl, 1-pentenyl, 3-penten-2-methyl-2-yl or 9-octadencen-1-yl, preferably vinyl and allyl and particularly preferentially vinyl.

$Y_1$ and $Y_2$ can be cycloalkyl having 5–8 C atoms, for example cyclopentyl or cyclohexyl. Cyclopentyl or cyclohexyl is preferred and cyclohexyl is particularly preferred.

$Y_1$ and $Y_2$ can be $C_6$–$C_{10}$ cycloalkylalkyl, such as cyclopentylethyl, cyclohexylmethyl or cyclooctylmethyl. Cyclopentylethyl and cyclohexylmethyl are preferred and cyclohexylmethyl is particularly preferred.

$Y_1$ and $Y_2$ can be $C_6$–$C_{14}$ aryl, such as phenyl or naphthyl, especially phenyl, or they can be aryl substituted by $C_1$–$C_8$ alkyl, for example methylphenyl, ethylphenyl, butylphenyl or octylphenyl. Methylphenyl and ethylphenyl are preferred and methylphenyl is particularly preferred.

$Y_1$ and $Y_2$ can be $C_7$–$C_{20}$ aralkyl, such as benzyl, α-phenylethyl or β-phenylethyl. Benzyl and α-phenylethyl are preferred and benzyl is particularly preferred.

$Y_1$ and $Y_2$ can be the group —$(CH_2)_m$—COO($C_{1-4}$alkyl), in which m is the number 1 to 6, for example methoxycarbonylmethyl, methoxycarbonylethyl, ethoxycarbonylmethyl, ethoxycarbonylethyl, n-butoxycarbonylmethyl, methoxycarbonylpropyl, ethoxycarbonylbutyl, propoxycarbonylpentyl or butoxycarbonylhexyl. Groups in which m is 1 to 2 are preferred, such as methoxycarbonylmethyl, ethoxycarbonylmethyl, n-butoxycarbonylmethyl, methoxycarbonylethyl and butoxycarbonylethyl. Ethoxycarbonylmethyl is particularly preferred.

If $Y_1$ is —$(CH_2)_m$—COO—($C_{1-4}$ alkyl), $Y_2$ can also be the group —$(CH_2)_m$—COO($C_{5-20}$ alkyl), and especially —$(CH_2)_m$—COO($C_{8-20}$ alkyl), in which m is as defined above, for example n-pentyloxycarbonylmethyl, 2-hexyloxycarbonylethyl, 3-heptyloxycarbonylmethyl, n-octyloxycarbonylethyl, 2-ethylhexyloxycarbonylmethyl, n-dodecyloxycarbonylethyl, n-tetradecyloxycarbonylmethyl or n-octadecyloxycarbonylmethyl. 2-Ethylhexyloxycarbonylmethyl, n-dodecyloxycarbonylethyl, n-tetradecyloxycarbonylmethyl or n-octadecyloxycarbonylmethyl is preferred. 2-Ethylhexyloxycarbonylmethyl and n-tetradecyloxycarbonylmethyl are particularly preferred.

Preferred compounds of the formula (I) are those in which $Y_1$ is —$(CH_2)_m$—COO ($C_{1-4}$ alkyl) and $Y_2$ is identical to $Y_1$ or is —$(CH_2)_m$—COO—($C_{5-20}$ alkyl) and R is hydrogen or methyl, m is the number 1 or 2 and n is the number 1.

Preferred compounds of the formula (I) are:

1. [(n—$C_{14}H_{29}$—S]$_2$Sn—($CH_2$—CH($CH_3$)—C(NH)—S—n—$C_{14}H_{29}$)$_2$
2. [(i—$C_8H_{17}$—S]$_3$Sn—$CH_2$—$CH_2$—C(NH)—S—i—$C_8H_{17}$
3. [(n—$C_{14}H_{29}$—OOC—$CH_2$—S]$_3$Sn—$CH_2CH_2$—C(NH)—S—$CH_2$—COO—$CH_2CH_3$
4. [(i—$C_8H_{17}$—OOC—$CH_2$—S]$_3$Sn—$CH_2CH_2$—C(NH)—S—$CH_2$—COO—$CH_2CH_3$
5. ($CH_3$—OOC—$CH_2$—S)$_3$Sn—$CH_2CH_2$—C(NH)—S—$CH_2$—COO—$CH_3$
6. ($CH_3CH_2$—OOC—$CH_2CH_2$—S)$_3$Sn—$CH_2CH_2$—C(NH)—S—$CH_2CH_2$—COO—$CH_2CH_3$

The invention also relates to a process for the preparation of compounds of the formula (I), which comprises reacting a compound of the formula (II)

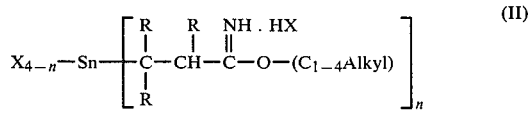

with a mercaptan $Y_2$—SH, in which formulae R, n and $Y_2$ are as defined above and X is chlorine, bromine or iodine, in the presence of a weak to medium strength base in an inert solvent.

Suitable inert solvents are, for example, ethers, hyrocarbons and halogenated hydrocarbons or acid amides, for example methylene chloride, chloroform, diethyl ether, tetrahydrofuran, toluene or dimethylformamide. Chloroform or toluene is preferred.

Suitable weak to medium strength bases are alkali metal carbonates and alkali metal bicarbonates, such as sodium carbonate and sodium bicarbonate, or tertiary amines, such as triethanolamine. Sodium bicarbonate is particularly suitable.

The reaction of the imino-ethers with mercaptans cna take place either in approximately stoichiometric amounts or with excess mercaptan.

The reaction temperature is in general −30° to 100° C. and preferably 20°–50° C. The reaction is advantageously carried out under normal pressure or a slight excess pressure.

The starting materials for the preparation of the mono-organo-tin compounds of the formula (I) are obtainable by direct reaction of a tin dihalide with an unsaturated nitrile of the formula (III)

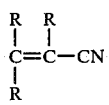
(III)

in which R is as defined above, and with hydrogen chloride, hydrogen bromide or hydrogen iodide, in the presence of an aliphatic alcohol having 1–4 C atoms.

The starting materials for the preparation of the di-organo-tin compounds of the formula (I) are obtainable by direct reaction of metallic tin with an unsaturated nitrile of the formula (III) and with hydrogen chloride, hydrogen bromide or hydrogen iodide, in the presence of an aliphatic alcohol having 1–4 C atoms.

In both processes, the reaction temperature is in general −30°to 100° C. and preferably 20°–50° C. The reaction is advantageously carried out under normal pressure or slight excess pressure.

In detail, the procedure is that the tin or the tin dihalide and the reactants are initially introduced, with or without solvents, and the hydrogen halide (preferably HCl) is passed in.

However, it is also possible initially to introduce the tin or the tin dihalide in the solvent and to add the reactants and the hydrogen halide gas at the same time. In this case it is advantageous to work by the counter-current principle and it is also possible to carry out the process by a continuous procedure.

Suitable solvents are the inert solvents indicated above.

The organo-tin compounds according to the invention are suitable for stabilising chlorine-containing thermoplastics.

The stabilisers can be added to the chlorine-containing thermoplastics in the customary amounts. Preferably 0.01 to 10, especially 0.1 to 5 and in particular 0.5 to 3% by weight are incorporated, based on the chlorine-containing thermoplastics.

The chlorine-containing thermoplastics used are preferably polymers or copolymers of vinyl chloride. Preferred polymers are suspension polymers and bulk polymers and washed emulsion polymers, i.e. emulsion polymers with a low emulsifier content. Suitable comonomers for the copolymers are, for example: vinylidene chloride, trans-dichloroethene, ethylene, propylene, butylene, maleic acid, acrylic acid, fumaric acid and itaconic acid.

Further suitable polymers are post-chlorinated polyolefins.

The stabilised thermoplastics are prepared by known processes, by incorporating the stabilisers according to the invention and, if desired, further stabilisers into the polymer. A homogeneous mixture of stabiliser and PVC can be obtained, for example, with the aid of a two-roll mixer at 150°–210° C. Depending on the intended use of the moulding composition, it is also possible to incorporate further additives before or at the same time as the incorporation of the stabiliser, such as lubricants, preferably montan waxes or glycerol esters, plasticisers, fillers, modifiers, such as additives imparting impact strength, pigments, light stabilisers, UV absorbers, antioxidants or further co-stabilisers, for example phosphites, epoxidised fatty acid esters or the metal derivates, such as barium, strontium, calcium, zinc, cadmium, lead, tin and magnesium, of phenols or carboxylic acids (fatty acids or epoxidised fatty acids). Mixtures of calcium carboxylates and zinc carboxylates, in which the carboxylate group can have 8 to 20 C atoms, have proved particularly advantageous. The thermoplastics can be processed to mouldings by the shaping processes customary for this purpose, for example by extrusion, injection moulding or calendering.

It is extremely surprising that the replacement of a functional radical by an imino-ether group has such a great influence on the stability to heat of the compounds according to the invention.

The following examples illustrate the invention. Parts are by weight.

EXAMPLE 1

(a) Preparation of the starting material:

1 mol (189.6 g) of dry $SnCl_2$, 1 mol (53.1 g) of acrylonitrile and 1 mol (46.1 g) of absolute ethanol in 800 ml of chloroform are initially introduced at 20° C. into a three-necked flask provided with a stirrer, a reflux condenser and a bubble counter. A stream of dry HCl gas is passed through the mixture, with stirring, and the steam is regulated so that the temperature does not exceed 55° C. After about 6 hours the reaction has ended (saturation with HCl). The precipitate formed is then filtered off with suction, washed with $CHCl_3$ and dried in vacuo at about 50° C.

The $^1H$ NMR spectrum is in agreement with the following structure:

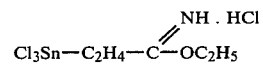

Analysis: $Sn^{2+}$ negative; Sn 32.9%; Cl 39.1%.

(b) Preparation of: (n—$C_{14}H_{29}$—OOC—CH$_2$—S—)$_3$Sn—CH$_2$CH$_2$—C(NH)—S—CH$_2$—COO—CH$_2$CH$_3$ 891.4 g of HS—CH$_2$—COO(n—$C_{14}$—H$_{29}$) are added to 291 g of the imino-ester obtained according to Example 1a) and the mixture is diluted with 1 l of $CHCl_3$. 290 g (including 10% excess) of $NaHCO_3$ are now added in portions, with stirring. The mixture is then refluxed for about 1 hour, cooled to about 20° C. and extracted with twice 1 l of water. The organic phase is dried over $Na_2SO_4$, concentrated and treated for about 15 minutes at 50°–60° C. under 0.5–1 mm Hg, produced with an oil pump. An oily, colourless liquid forms.

$n_D^{20}$ = 1.4950; Analysis: Sn 9.2%

EXAMPLE 2

Static heat test

A dry blend consisting of 100 parts of PVC (Solvic 264 GA), 0.2 part of lubricant (Wax E from Deutsche Solvay-Werke) and 1.7 parts of the stabiliser from Example 1 is rolled on mixing rolls for 5 minutes at 180° C. and 0.3 mm thick test film pieces are then taken.

The film samples are exposed to heat in an oven at 180° C. and every 15 minutes the yellowness index (YI) of a sample is determined in accordance with ASTM D1925-70:

| Yellowness Index (Y.I.) after exposure time in minutes: | | | | |
|---|---|---|---|---|
| Time | 15' | 30' | 45' | 60' | 75' |
| Y.I. | 11.8 | 16.3 | 40.1 | 79.7 | 98.7 |

What is claimed is:

1. A compound of the formula (I)

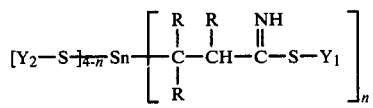
(I)

in which the radicals R independently of one another are hydrogen or $C_1$-$C_{14}$ alkyl and $Y_1$ and $Y_2$ are both identical and are $C_1$-$C_{20}$ alkyl, $C_2$-$C_{20}$ alkenyl, $C_5$-$C_8$ cycloalkyl, $C_6$-$C_{10}$ cycloalkylalkyl, $C_6$-$C_{14}$ aryl, which is unsubstituted or substituted by $C_1$-$C_8$ alkyl, or $C_7$-$C_{20}$ aralkyl or —$(CH_2)_m$—COO ($C_{1-4}$ alkyl), or if $Y_1$ is —$(CH_2)_m$—COO—($C_{1-4}$ alkyl), $Y_2$ can also be the group —$(CH_2)_m$—COO($C_{5-20}$ alkyl), and in which m is a number from 1 to 6 and n is 1 or 2.

2. A compound according to claim 1, of the formula (I), in which $Y_1$ is —$(CH_2)_m$—COO($C_{1-4}$ alkyl) and $Y_2$ is identical to $Y_1$ or is —$(CH_2)_m$—COO($C_{5-20}$ alkyl) and m is a number from 1 to 6.

3. A compound according to claim 1, of the formula (I), in which R is hydrogen or methyl.

4. A compound according to claim 1, of the formula (I), in which n is the number 1 and m is 1 or 2.

5. A compound according to claim 1, of the formula (I), in which the radicals R are hydrogen, $Y_1$ is the group —$CH_2$—$COOCH_2CH_3$ and $Y_2$ is the group —$CH_2$—COO($C_{8-20}$ alkyl).

6. The compound according to claim 1, of the formula (I) in which the radicals R are hydrogen, $Y_1$ is —$CH_2$—$COOCH_2CH_3$, $Y_2$ is —$CH_2$—COO—$(CH_2)_{13}CH_3$ and n is 1.

7. A process for the preparation of a compound of formula (I), according to claim 1,

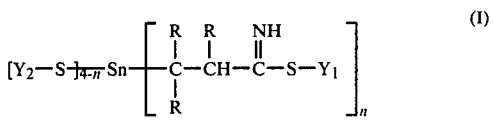
(I)

in which the radicals R independently of one another are hydrogen or $C_1$-$C_4$ alkyl and $Y_1$ and $Y_2$ are both identical and are $C_1$-$C_{20}$ alkyl, $C_2$-$C_{20}$ alkenyl, $C_5$-$C_8$ cycloalkyl, $C_6$-$C_{10}$ cycloalkylalkyl, $C_6$-$C_{14}$ aryl, which is unsubstituted or substituted by $C_1$-$C_8$ alkyl, or $C_7$-$C_{20}$ aralkyl or —$(CH_2)_m$—COO ($C_{1-4}$ alkyl), or if $Y_1$ is —$(CH_2)_m$—COO—($C_{1-4}$ alkyl), $Y_2$ can also be the group —$(CH_2)_m$—COO($C_{5-20}$ alkyl), and in which m is a number from 1 to 6 and n is 1 or 2;

which comprises reacting at a temperature of −30° C. to 100° C. a compound of formula (II)

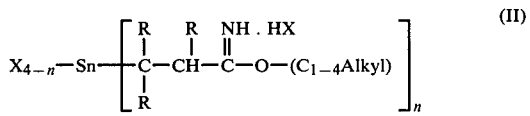
(II)

wherein X is chlorine, bromine or iodine, with an approximately stoichiometric to slight excess molar amount of a mercaptan $Y_2$—SH, in the presence of a slight excess molar amount of a weak to medium strength base in an inert solvent.

8. A halogen-containing thermoplastic containing as a heat stabilizer an effective amount of a compound of formula (I) according to claim 1.

9. A process for the preparation of a compound of the formula (I) according to claim 7, wherein the weak base used for the reaction is an alkali metal bicarbonate.

* * * * *

UNITED STATES PATENT AND TRADEMARK OFFICE
CERTIFICATE OF CORRECTION

PATENT NO. : 4,285,856
DATED : AUGUST 25, 1981
INVENTOR(S) : WOLFGANG WEHNER ET AL

It is certified that error appears in the above—identified patent and that said Letters Patent is hereby corrected as shown below:

CLAIM 1, COLUMN 5, LINE 23 reads:

"are hydrogen or $C_1-C_{14}$ alkyl and $Y_1$ and $Y_2$ are both"

Should read:

-- are hydrogen or $C_1-C_4$ alkyl and $Y_1$ and $Y_2$ are both --

Signed and Sealed this

Twenty-second Day of December 1981

|SEAL|

*Attest:*

*Attesting Officer*

GERALD J. MOSSINGHOFF
*Commissioner of Patents and Trademarks*